(12) United States Patent
McGuckin, Jr.

(10) Patent No.: US 8,109,940 B2
(45) Date of Patent: *Feb. 7, 2012

(54) BREAST SURGERY METHOD AND APPARATUS

(75) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/803,061

(22) Filed: Jun. 18, 2010

(65) Prior Publication Data

US 2010/0262159 A1    Oct. 14, 2010

Related U.S. Application Data

(60) Continuation of application No. 11/389,753, filed on Mar. 27, 2006, now Pat. No. 7,753,920, which is a division of application No. 09/982,359, filed on Oct. 18, 2001, now Pat. No. 7,052,501, which is a continuation of application No. 09/838,722, filed on Apr. 19, 2001, now Pat. No. 6,589,252, which is a division of application No. 09/122,185, filed on Jul. 23, 1998, now Pat. No. 6,280,450.

(60) Provisional application No. 60/053,664, filed on Jul. 24, 1997.

(51) Int. Cl.
*A61B 17/22* (2006.01)
(52) U.S. Cl. ........................................................ 606/114
(58) Field of Classification Search .................. 606/114, 606/37, 39, 113, 127, 128, 159, 180
See application file for complete search history.

(56) References Cited

U.S. PATENT DOCUMENTS

| | | |
|---|---|---|
| 2,816,552 A | 12/1957 | Hoffman |
| 3,320,957 A | 5/1967 | Sokolik |
| 4,011,872 A | 3/1977 | Komiya |
| 4,503,855 A | 3/1985 | Maslanka |
| 4,611,594 A | 9/1986 | Grayhack et al. |
| 4,616,656 A | 10/1986 | Nicholson et al. |
| 4,935,027 A | 6/1990 | Yoon |
| 4,966,604 A | 10/1990 | Reiss |
| 4,976,711 A | 12/1990 | Parins et al. |
| 4,997,435 A | 3/1991 | Demeter |
| 5,078,716 A | 1/1992 | Doll |
| 5,100,423 A | 3/1992 | Feamot |
| 5,176,128 A | 1/1993 | Andrese |
| 5,176,687 A * | 1/1993 | Hasson et al. ................ 606/114 |
| 5,190,561 A | 3/1993 | Graber |
| 5,197,968 A | 3/1993 | Clement |
| 5,201,741 A | 4/1993 | Dulebohn |
| 5,207,675 A | 5/1993 | Canady |

(Continued)

FOREIGN PATENT DOCUMENTS

WO    WO 8905608    6/1989

(Continued)

*Primary Examiner* — Pedro Philogene
(74) *Attorney, Agent, or Firm* — Neil D. Gershon

(57) ABSTRACT

A surgical apparatus for cutting a tissue mass comprising an elongated housing having a distal portion, a rotatable shaft positioned in the elongated housing, and a plurality of flexible electrocautery cutting blades extending from the housing, wherein the plurality of cutting blades are radially expandable from a first position defining a first diameter to a second larger diameter and the blades are rotatable and transmit electrical energy to cut the tissue mass.

14 Claims, 8 Drawing Sheets

U.S. PATENT DOCUMENTS

| | | |
|---|---|---|
| 5,224,488 A | 7/1993 | Neuffer |
| 5,281,238 A | 1/1994 | Chin et al. |
| 5,282,484 A * | 2/1994 | Reger .......................... 128/898 |
| 5,318,576 A * | 6/1994 | Plassche et al. .............. 606/159 |
| 5,353,804 A | 10/1994 | Komber et al. |
| 5,370,647 A | 12/1994 | Graber et al. |
| 5,376,100 A * | 12/1994 | Lefebvre ....................... 606/180 |
| 5,397,320 A | 3/1995 | Essig et al. |
| 5,417,697 A | 5/1995 | Wilk et al. |
| 5,437,665 A | 8/1995 | Munro |
| 5,439,474 A | 8/1995 | Li |
| 5,486,183 A | 1/1996 | Middleman et al. |
| 5,496,330 A | 3/1996 | Bates et al. |
| 5,514,153 A | 5/1996 | Bonutti |
| 5,524,633 A | 6/1996 | Heaven et al. |
| 5,573,008 A | 11/1996 | Robinson et al. |
| 5,632,746 A | 5/1997 | Middleman et al. |
| 5,649,547 A | 7/1997 | Richart et al. |
| 5,653,684 A | 8/1997 | Laptewicz |
| 5,709,697 A | 1/1998 | Ratcliff et al. |
| 5,735,289 A | 4/1998 | Pfeffer et al. |
| 5,746,747 A | 5/1998 | McKeating |
| 5,759,187 A | 6/1998 | Nakao et al. |
| 5,794,626 A | 8/1998 | Kieturakis |
| 5,810,806 A | 9/1998 | Ritchart et al. |
| 5,820,629 A | 10/1998 | Cox |
| 5,836,953 A | 11/1998 | Yoon |
| 5,853,374 A | 12/1998 | Hart et al. |
| 5,871,454 A | 2/1999 | Majlessi |
| 5,885,278 A | 3/1999 | Fleischman |
| 5,895,361 A | 4/1999 | Turturro |
| 5,895,392 A | 4/1999 | Riek et al. |
| 5,895,417 A | 4/1999 | Pomeranz et al. |
| 5,897,567 A | 4/1999 | Ressemann et al. |
| 5,904,679 A | 5/1999 | Clayman |
| 5,947,964 A | 9/1999 | Eggers et al. |
| 5,989,266 A | 11/1999 | Foster |
| 6,007,495 A | 12/1999 | Matula |
| 6,036,698 A | 3/2000 | Fawzi et al. |
| 6,059,734 A | 5/2000 | Yoon |
| 6,068,603 A | 5/2000 | Suzuki |
| 6,080,113 A | 6/2000 | Heneveld et al. |
| 6,080,114 A | 6/2000 | Russin |
| 6,096,053 A | 8/2000 | Bates |
| 6,106,524 A | 8/2000 | Eggers et al. |
| 6,165,137 A | 12/2000 | Milliman et al. |
| 6,171,315 B1 | 1/2001 | Chu et al. |
| 6,179,860 B1 | 1/2001 | Fulton et al. |
| 6,216,043 B1 | 4/2001 | Swanson et al. |
| 6,221,006 B1 | 4/2001 | Dubrul et al. |
| 6,261,241 B1 | 7/2001 | Burbank et al. |
| 6,280,450 B1 * | 8/2001 | McGuckin, Jr. .............. 606/114 |
| 6,312,428 B1 | 11/2001 | Eggers et al. |
| 6,331,166 B1 | 12/2001 | Burbank et al. |
| 6,344,026 B1 | 2/2002 | Burbank et al. |
| 6,375,661 B2 | 4/2002 | Chu et al. |
| 6,454,727 B1 | 9/2002 | Burbank et al. |
| 6,471,700 B1 | 10/2002 | Burbank et al. |
| 6,471,709 B1 | 10/2002 | Fawzi et al. |
| 6,530,923 B1 | 3/2003 | Dubrul et al. |
| 6,540,693 B2 | 4/2003 | Burbank et al. |
| 6,589,252 B2 * | 7/2003 | McGuckin, Jr. .............. 606/114 |
| 6,960,172 B2 | 11/2005 | McGuckin et al. |
| 7,052,501 B2 * | 5/2006 | McGuckin, Jr. .............. 606/114 |
| 7,753,920 B2 * | 7/2010 | McGuckin, Jr. .............. 606/114 |
| 2001/0000348 A1 | 4/2001 | Chu et al. |

FOREIGN PATENT DOCUMENTS

| | | |
|---|---|---|
| WO | WO 9502370 | 1/1995 |
| WO | WO 9944506 | 9/1999 |
| WO | WO 0020822 | 4/2000 |
| WO | WO 0074561 | 12/2000 |
| WO | WO 0128445 | 4/2001 |
| WO | WO 0128446 | 4/2001 |

* cited by examiner

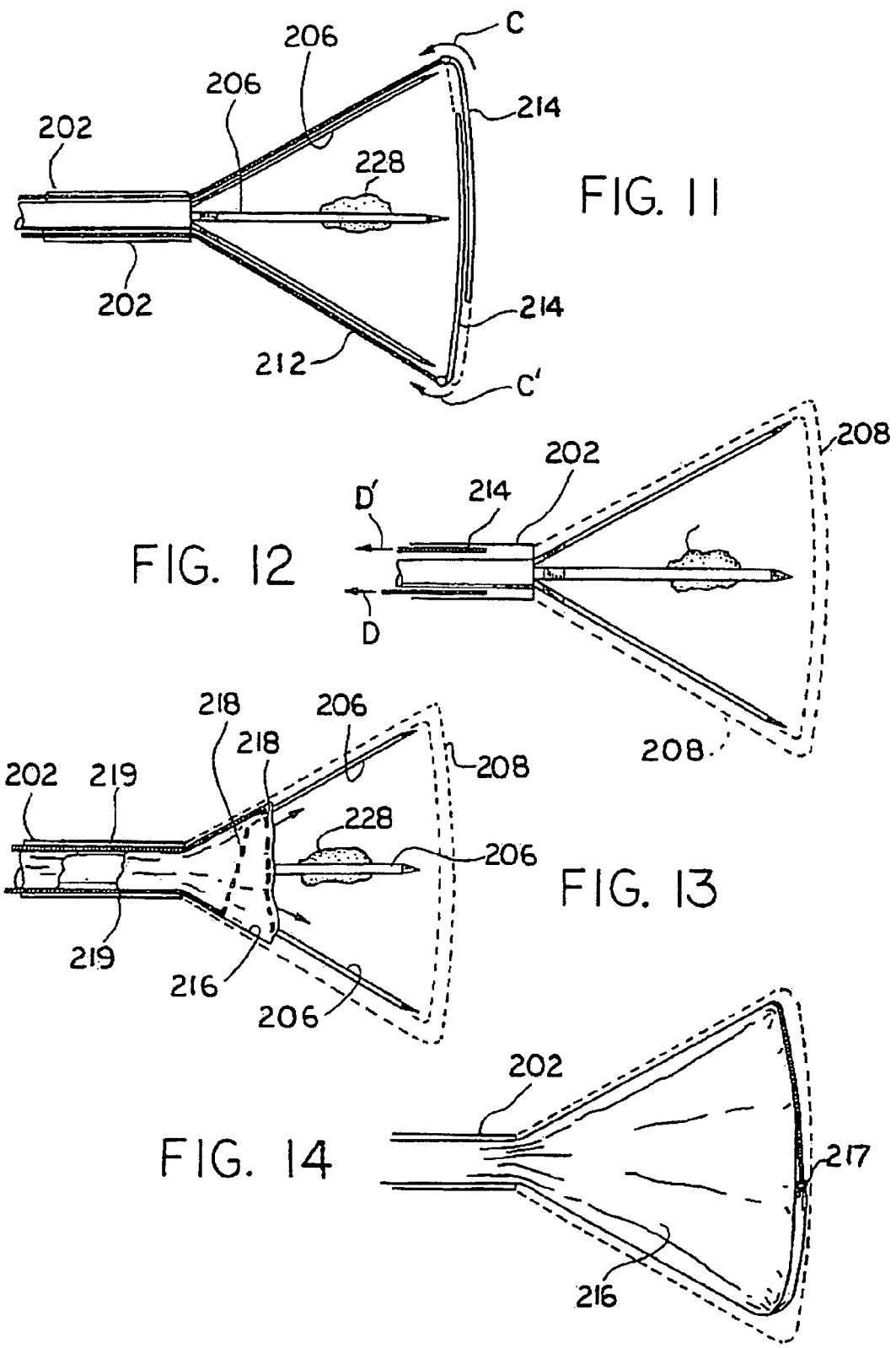

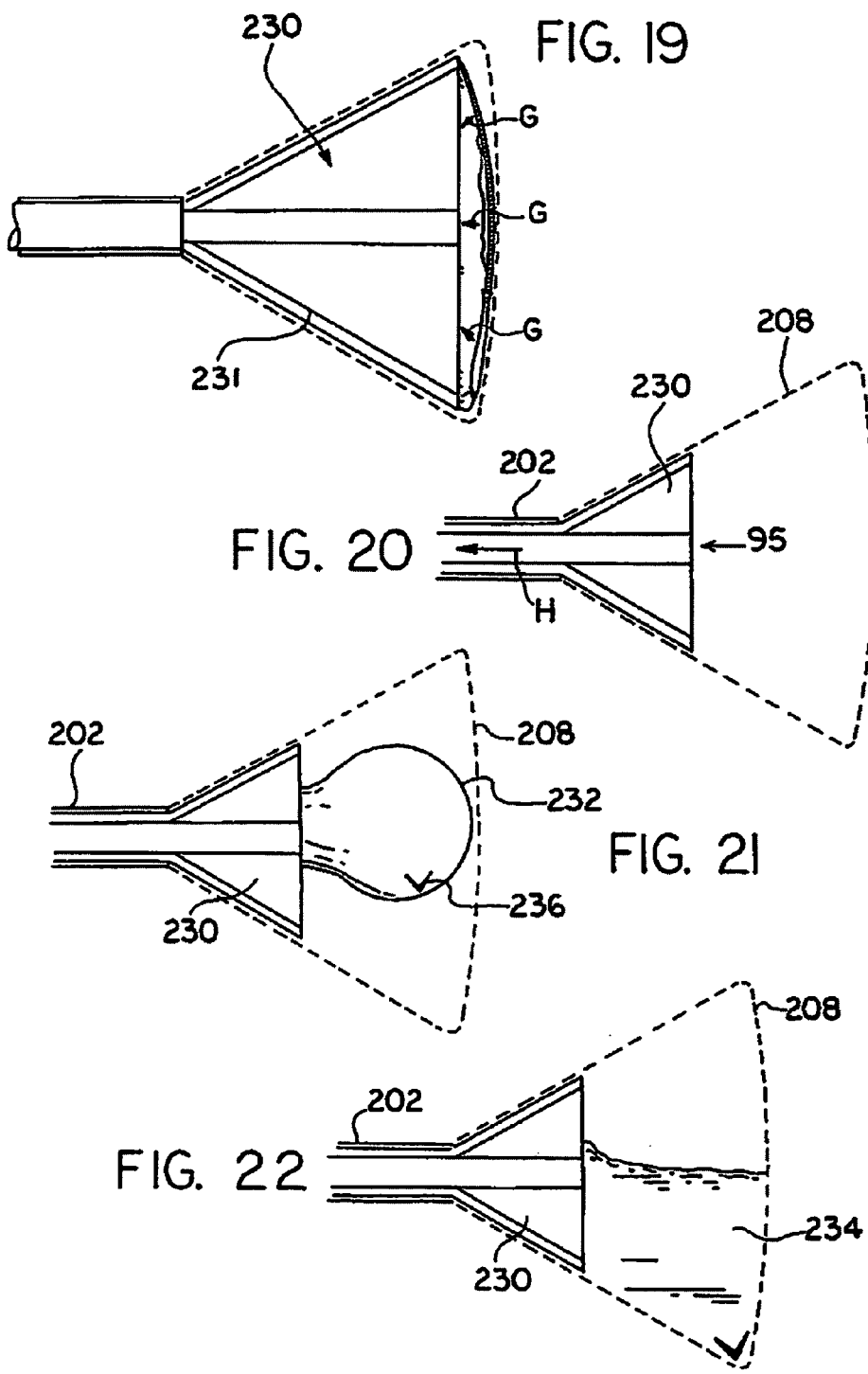

BREAST SURGERY METHOD AND APPARATUS

CROSS-REFERENCE TO RELATED PATENT APPLICATION

This application is a continuation of prior application Ser. No. 11/389,753 filed on Mar. 27, 2006, now U.S. Pat. No. 7,753,920 which is a divisional of U.S. patent application Ser. No. 09/982,359, filed on Oct. 18, 2001, now U.S. Pat. No. 7,052,501 which is a continuation of patent application Ser. No. 09/838,722, filed Apr. 19, 2001, now U.S. Pat. No. 6,589,252, which is a divisional of U.S. patent application Ser. No. 09/122,185, filed Jul. 23, 1998, now U.S. Pat. No. 6,280,450, which claims priority from provisional application 60/053,664, filed Jul. 24, 1997. The entire contents of each of these applications is incorporated herein by reference.

FIELD OF THE INVENTION

This invention relates to surgical apparatus and methods for obtaining a subcutaneous target mass having varied shape and dimension.

BACKGROUND OF THE INVENTION AND DESCRIPTION OF THE PRIOR ART

Modern medical diagnostics increasingly rely on complex imaging technologies to identify abnormal conditions and/or masses within the human body. Such technologies as magnetic resonance imaging (MRI), ultrasonics, computerized axial tomography (CAT scan), and mammogram x-rays, aid medical personnel in the initial identification of areas within the body exhibiting potentially dangerous, abnormal biological activity. The beneficial aspect of these technologies is their ability to image biological structures interior to the human body, providing a non-invasive tool useful in facilitating preliminary diagnosis and treatment of detected anomalies.

Detected subcutaneous biological growths, masses, etc. once identified generally require complete surgical excision or at the very least an open biopsy procedure.

Small masses such as calcifications encountered in breast tissue are generally removed in their entirety. The process of excising the mass is an invasive process, performed either during exploratory surgery or utilizing specifically designed surgical apparatus. The retrieved specimen is subsequently pathologically analyzed to determine its biological properties, i.e. benign or malignant.

Several types of apparatus are known for use in removing portions of subcutaneous masses in breast tissue targeted by these imaging techniques. However, these apparatus generally either obtain only small tissue specimens from the main mass or cause significant surface scarring due to the size of the incision necessary to remove the mass with a safe resection margin.

One type of specimen retrieval is performed with needle aspiration devices. These devices have a needle with an end hole. The needle is advanced to a desired location where a sample specimen is obtained via suction. Size and quality of specimens obtained by these devices are often poor, requiring multiple sampling of each desired target mass. Moreover, tissue encountered along the path to the desired location is unavoidably removed. A hollow channel is created upon withdrawal of the device from the patient, thereby allowing "seeding" of the hollow channel removal tract with abnormal cells. Some needle systems utilize an enlarged needle end hole, creating a boring probe which obtains a greater portion of tissue. This lessens the likelihood that the specimen will be too small but increases the amount of surface scarring due to the larger size incision required.

The percutaneous incisions needed when multiple needle channels or large needle bore channels are used often result in significant scarring, dimpling and disfigurement of surface tissue.

Needle side cutting devices have a blade extending around the circumference of a hollow needle shaft. The shaft and blade are axially rotated around the skin entry site, allowing a larger overall specimen to be excised. Target tissue is sliced and a non-contiguous specimen is obtained due to the spiral blade path. While these needle side cutting devices facilitate capture of larger sample specimens, they require resection of a relatively large core of tissue between the incision and the specimen desired to be resected. Additionally, needle side cut devices result in irregularly shaped specimens and subcutaneous cavities having irregular and/or bleeding margins.

Hence, the known devices are particularly ill suited in retrieving tissue masses from the female breast, due to the interest in preserving cosmetic integrity of the surface tissue as well as the inability of the known devices to remove most masses/calcifications during a single application.

SUMMARY OF THE INVENTION

This invention provides surgical apparatus and methods where size and shape of subcutaneous tissue identified for excision is minimally dependent on dimensions of the percutaneous incision. The apparatus and methods have specific utility in breast surgery.

In one of its aspects this invention provides apparatus for excision of the subcutaneous target tissue mass through a cutaneous incision smaller than maximum transverse dimension of the tissue mass excised where the apparatus includes an axially elongated member including cutaneous tissue piercing means at one end and means connected to the elongated member and being radially expandable relative thereto for cutting a circumferential swath of radius greater than maximum transverse dimension of the elongated member and greater than maximum transverse cross-sectional dimension of the target tissue mass in order to separate the target tissue mass from surrounding tissue for excision thereof through the incision. The apparatus may further include an expandable aseptic shield concentric with the elongated member and axially slidably advanceable over the cutting means when in the radially expanded configuration, to collectibly bag the target tissue mass detached from the patient by the cut circumferential swath, for aseptic removal in an axial direction together with the elongated member through the incision resulting from entry of the cutaneous tissue piercing means.

The apparatus may yet further include a sheath which is axially slidably concentric with the elongated member and connected to first ends of the cutting means for expanding the cutting means from generally linear and axial orientation to a curved basket-like orientation by axial movement relative to the elongated member.

In yet another of its aspects the invention provides apparatus for excision of a sub-cutaneous target tissue mass through a cutaneous incision smaller than maximum transverse dimension of the tissue mass excised where the apparatus includes an axially elongated member through which cutaneous tissue piercing means may be extended to emerge at one end thereof. The apparatus further includes means insertable through the elongated member which is radially expandable relative to the elongated member for cutting a conical swath having base radius greater than maximum transverse dimension of the elongated member and greater than maximum transverse cross-sectional dimension of the target tissue mass, for separating the target tissue mass from surrounding tissue for removal thereof through the incision. In this embodiment of the invention the apparatus further preferably includes expandable aseptic shield means insertable through the elongated member and advanceable over the path of the cutting means to radially expand and collectibly bag the tissue mass detached from a patient by the conical swath cutting for aseptic removal in an axial direction through the elongated member and the incision resulting from entry of the cutaneous tissue piercing means.

In one of its aspects this invention preferably provides such apparatus having a piercing segment for penetrating a percutaneous entrance incision. The forward edge of the piercing segment preferably separates breast tissue in the path of the target tissue to be excised. The piercing segment preferably passes through the specimen to be excised, delivering an associated preferably circular array of preferably highly flexible cutting blades to the interior identified subcutaneous breast growth.

The circular array of preferably flexible cutting blades is preferably radially expanded by action of an attached actuating shaft. The blades radially expand to preferably cut by electro-cauterizing the breast tissue as they rotate around a defined periphery. The blades preferably outwardly expand to envelope the target tissue specimen and axially rotate to separate the target tissue growth from surrounding breast tissue. The target tissue growth is excised from surrounding breast tissue outisde the periphery of the circular blade path and is preferably secured by a snaring membrane placed riding over the circular array of flexible cutting blades.

The membrane is preferably secured over the blade array through an integral drawstring assembly contracting the mouth of the snaring membrane. The membrane-encased blade array is preferably drawn into a recovery sheath and compressed for aseptic removal from the excision site.

In a method aspect this invention removes subcutaneous breast growths. A percutaneous surface incision is prepared for reception of surgical apparatus. Through use of suitable medical imaging technologies, the cutting apparatus device is guided to the area of the target subcutaneous breast growth while preferably maintaining a fixed subcutaneous reference point. A circular array of blades is then preferably radially expanded, preferably forming a cutting basket having dimensions larger than the target subcutaneous breast growth. Radial expansion and rotation of the electro-cauterizing blades separates the targeted growth from surrounding tissue. A snaring membrane advances over the blade array and is secured by an integral drawstring assembly. A recovery sheath compresses the membrane, encasing the target growth as it is withdrawn from the subcutaneous breast cavity. As a result, a growth which is large relative to the entrance incision is excised. In another of its method aspects this invention provides a procedure for excision of a sub-cutaneous target tissue mass through a cutaneous incision which is smaller than maximum transverse dimension of the target tissue mass to be excised where the procedure includes an advancing tissue piercing means towards a patient to create an incision in the patient's skin, slidably advancing cutting means through the incision and into sub-cutaneous tissue until in position to radially expand and cut a circumferential swath around the target tissue mass larger than the incision, cutting a circumferential swatch around the target tissue mass thereby separating the target mass from the surrounding tissue, slidably advancing flexible aseptic containment means over the separated target tissue mass to a position of closure about the target tissue mass and withdrawing the flexible aseptic containment means, with the target tissue mass aseptically contained therewithin, through the incision. The method may further include collapsing the cutting means after cutting the swath.

In yet another of its method aspects, this invention provides a procedure for excision of sub-cutaneous target tissue mass through a cutaneous incision smaller than maximum transverse dimension of the target tissue mass to be excised where the procedure includes advancing tissue piercing means towards the patient to create an incision in the patient's skin, slidably advancing cutting means through the incision and into sub-cutaneous tissue until in position to gradually radially expand and cut a conical swath about the target tissue mass larger than the incision thereby separating the target tissue mass from the surrounding tissue, slidably advancing flexible aseptic containment means over the separated target tissue mass to a position of closure around the target tissue mass and withdrawing the flexible aseptic containment means with the target tissue mass aseptically contained therewithin through the incision. The invention in this aspect preferably further includes radially inwardly collapsing the cutting means, which is preferably wire, after cutting the conical swath and may yet further include radially inwardly cutting tissue along the base of said cone by a passage of the cutting wire therethrough and thereafter closing flexible aseptic containment means over about the periphery of the cone and the target tissue mass contained therewithin.

BRIEF DESCRIPTION OF THE DRAWINGS

FIG. 11 is a side view of the apparatus shown in FIG. 10 with the cutting wire fully deployed.

FIG. 12 is a side view of the preferred embodiment of the apparatus depicting a new cutting wire retraction.

FIG. 13 is a side view of the preferred embodiment of the apparatus showing advancement of the bagging structure.

FIG. 14 is a side view of the preferred embodiment with tissue containment bagging completed.

FIG. 19 is a side view similar to FIG. 16 but showing the containment sheath fully deployed.

FIG. 20 is a side view similar to FIG. 19 but showing the containment sheath being withdrawn.

FIG. 21 is a side view similar to FIG. 19 showing optional use of a medicament bag and a radiological marker FIG. 22 is a side view similar to FIG. 19 showing optional use of liquid medication supported in part by the containment sheath.

DETAILED DESCRIPTION OF THE PREFERRED EMBODIMENTS

This invention provides surgical apparatus and methods for excision of percutaneous breast tissue. The apparatus has the capability to pass through an incision substantially smaller than the maximum percutaneous target specimen dimension occupying an excision site. In one embodiment the surgical apparatus preferably cuts the target tissue with an electro-cauterizing, circular array of flexible cutting blades, preferably collecting the specimen within the periphery of an expandable blade path; thus the complete growth is preferably obtained in a single procedure. The tissue is preferably returned as a complete specimen or, alternatively, in segments within a snaring membrane. A recovery sheath is preferably positioned to further encase and compress the blade array upon contraction.

Figure 1:
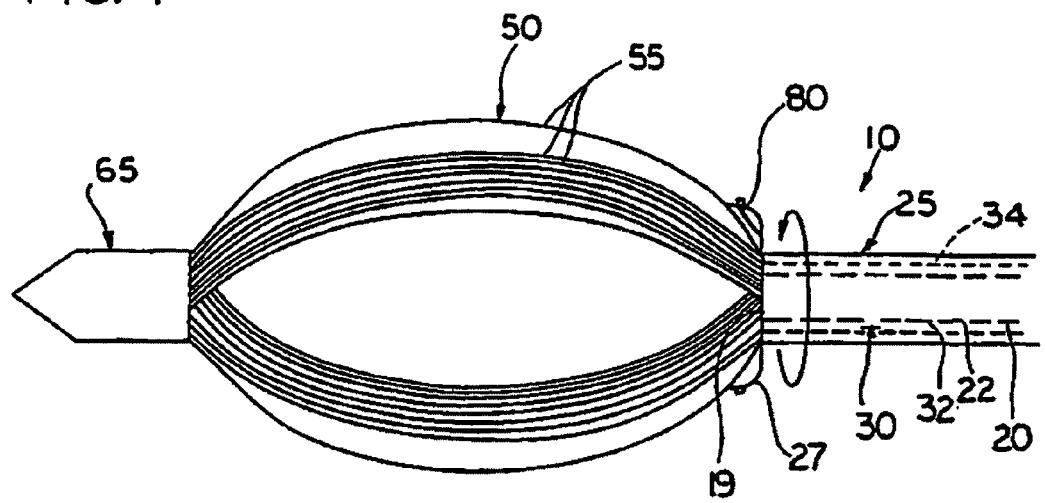
FIG. 1 is a side view one embodiment of apparatus manifesting aspects of the invention with the cutting blades in radially expanded condition.

Referring to FIG. 1, the illustrated embodiment of surgical apparatus 10 includes an inner rotatable shaft 20, a tubular recovery sheath 25, a snaring membrane 30, a circular array of radially flexible and expandable cutting blades generally designated 50, a membrane drawstring 80, a membrane mouth section 27 of recovery sheath 25, a power source 15 and a tissue piercing member 65.

Membrane 30 preferably has an inner surface 32 coaxially parallel with shaft 20, and an outer surface 34. Inner surface 32 of membrane 30 preferably slidably facingly contacts the outside surface 22 of shaft 20. Membrane 30 is adjustably positioned in either the distal or proximate direction through the proximate end of shaft 20.

Tubular recovery sheath 25 preferably includes a distal pleated mouth section 27, an outer surface 45, and an inner surface 60 facingly coaxially contacting membrane 30. Inner surface 60 slidably engages outer surface 34 of membrane 30. shaft 20 defines a rotational axis 12.

Shaft 20 rotates as denoted by arrow 12. Rotatable shaft 20 of surgical apparatus 10 is preferably rotated manually, through mechanical hand control. However, shaft 20 may be operably linked with an electrical motor, not shown, which may be driven by power source 15.

Circular cutting blade 50 includes individual flexible blades 55 which are preferably anchored between piercing member 65 and proximate end of shaft 20. Blades 55 are preferably electro-cauterizing, heated by electrical power source 15.

The materials utilized to construct surgical apparatus 10 are preferably radiopaque to be visible using modern medical imaging systems.

Figure 2:
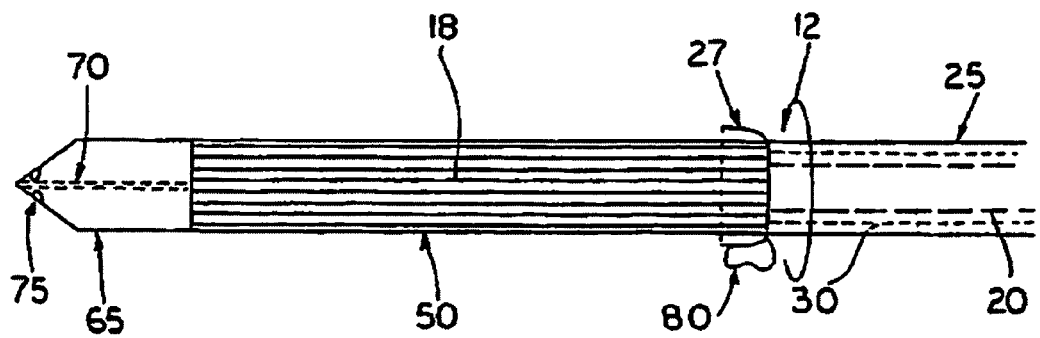
FIG. 2 is a side view of the surgical apparatus illustrated in FIG. 1 of the cutting blades in their non-expanded condition.

Referring to FIG. 2, surgical apparatus 10 is shown with individual flexible blades 55 in their non-expandable, tissue insertion orientation. In this insertion orientation the blades are parallel with and of slightly smaller diameter than tubular recovery sheath 25. Tubular recovery sheath 25 includes a snaring membrane 30 having a mouth section 27 and a drawstring 80, for drawing membrane 30 closed once it has been opened. Drawstring 80 is positioned along the distal margin of mouth section 27.

Mouth section 27 of membrane 30 expands outwardly in response to pulling of a polyvinyl tab or ripcord upon reaching the excision site. The polyvinyl tab or ripcord is preferably at the end of shaft 20 to the right, which is not shown in the drawing. The polyvinyl tab or ripcord is not visible in the drawing.

Recovery sheath 25 is preferably advanced over circular array of cutting blades 50 and preferably secured in place around the cutting blades and the excised specimen by pulling the drawstring towards the proximate end of shaft 20.

Figure 3:
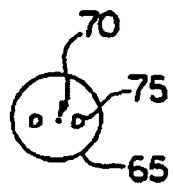
FIG. 3 is a front view of a modified version of the apparatus illustrated in FIGS. 1 and 2 with the cutting blades in a non-expanded condition as illustrated in FIG. 2.

Referring now to FIG. 3, piercing segment 65 is formed to separate subcutaneous tissue in the path between the surface incision and the growth.

Figure 4:
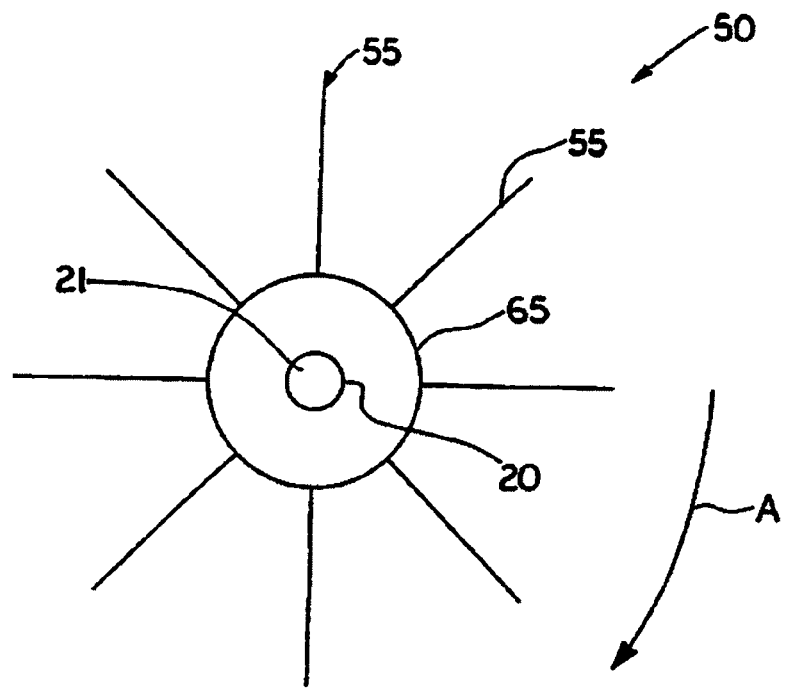
FIG. 4 is a front view of a modified version of the apparatus illustrated in FIGS. 1 through 3 with the cutting blades in their radially expanded condition as illustrated generally in FIG. 1.

FIG. 3 and FIG. 4 show a modification of the embodiment of surgical apparatus 10 illustrated in FIGS. 1 and 2. In the modification illustrated in FIGS. 3 and 4, shaft 20 includes an interior channel 21 extending forwardly through the center of the cutting blade circular array 50 and connecting with piercing membrane 65. A shaft stem section which is not shown connects to a dye port 70 in piercing member 65 for optional delivery of marking fluid to subcutaneous areas. Dye port 70 enables operators of apparatus 10 to deliver marking substances to the subcutaneous excision site. Alternatively, a titanium clip can be ejected from a clip fastening surface 75 for marking excision sites for future medical imaging analysis.

As shown in FIG. 4, the circular array 50 of cutting blades 55 expands radially upon relative moment of shaft 20 in the direction of piercing member 65, defining a cutting orientation. Flexible cutting blades 55 are preferably electro-cauterizing, cutting as they outwardly expand and as they rotate after radially outward expansion. Upon rotation of flexible cutting blades 55 in the direction indicated by arrow A in FIG. 4, the target tissue growth is separated from the surrounding subcutaneous breast tissue and remains within the periphery of the circular blade path.

As variations, the circular array of flexible cutting blades 50 may employ radially expandable ultrasonic cutting means, referred to as "harmonic scalpels", or laser cutting means.

Figure 5:
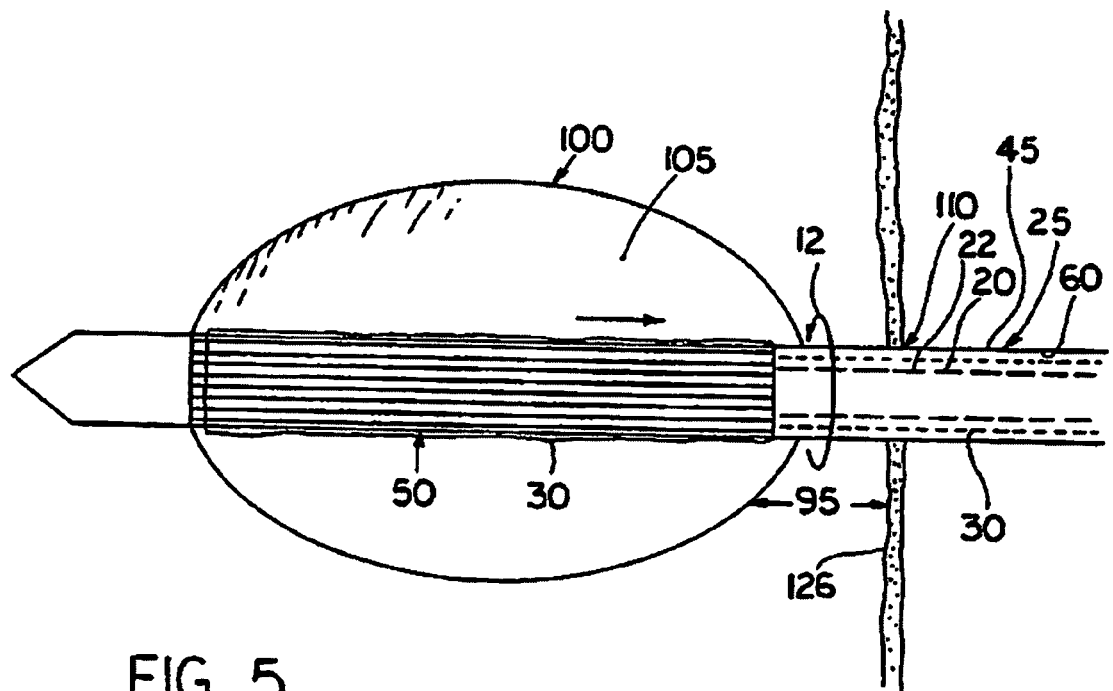
FIG. 5 is a broken schematic partially sectioned view of female breast tissue with the apparatus illustrated in FIGS. 1 through 4 in position within the breast in the process of removing a target tissue mass from the breast with the target tissue mass encased within an aseptic shield portion of the apparatus.

The method of excising subcutaneous breast target tissue growths is shown in FIG. 5. In FIG. 5 the edges of a surgical site where a growth has been removed is indicated as 100; removal of the growth has created subcutaneous cavity 105. As shown, subcutaneous cavity 105 is separated from a surface incision 126 by an excision distance 95.

In preparation for removing the subcutaneous breast tissue growth, percutaneous tissue is cut to produce an incision 126. A piercing member 65 of surgical apparatus 10 is placed at incision 126. An excision path is created by forcing piercing member 65 through the subcutaneous breast tissue between the percutaneous incision 126 and the identified target tissue growth. The target tissue growth is the desired excision site which is visualized via a medical imaging system such as ultrasound or mammography. The tip of surgical apparatus 10 is advanced until the piercing segment passes through the growth to be excised.

Once apparatus 10 is properly positioned relative to the target tissue mass as indicated by the medical imaging system, the proximate end of shaft 20 is urged towards piercing member 65. Flexible cutting blades 55 radially expand to define subcutaneous margin 100. The array of flexible cutting blades 50 is then rotated about the shaft axis as indicated by arrow 12, separating the target tissue growth along margin 100.

Membrane 30 is then advanced over the circular array of cutting blades 50 and secured by pulling integral drawstring 80 to the right in FIG. 5 towards the end of shaft 20. Drawstring 80 secures the distal margin of membrane 30. The mouth 27 of sheath 25 is expanded by the polyvinyl pull tab when drawn towards the end of shaft 20.

Circular array of cutting blades 55, now encased by membrane 30, is drawn into the mouth of snaring sheath 25 and removed from subcutaneous cavity 105.

Figure 6:
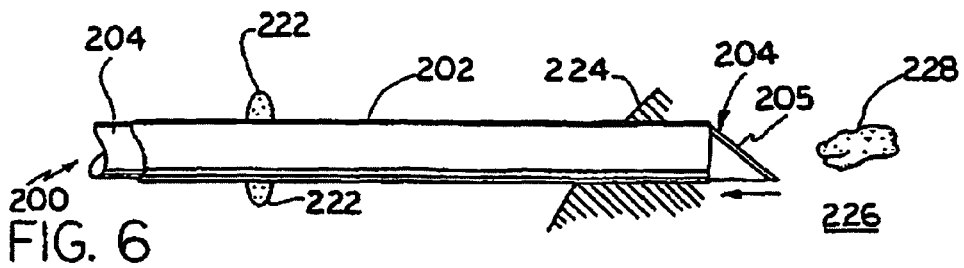
FIG. 6 is a side view of a portion of apparatus according one preferred embodiment of the invention shown in the course of practicing a preferred method aspect of the invention.
Figure 7:
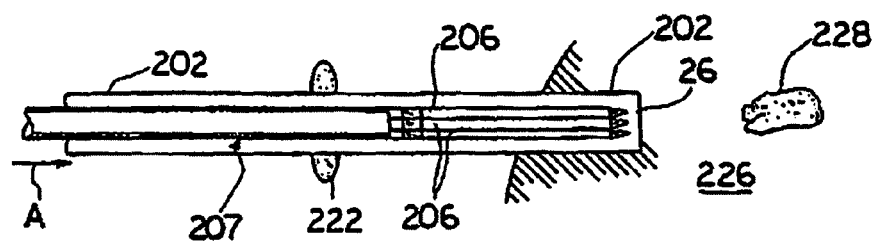
FIG. 7 is a side view of a part of the apparatus illustrated in FIG. 6 showing additional parts of one preferred apparatus embodiment of the invention in the course of practicing the inventive method.
Figure 8:
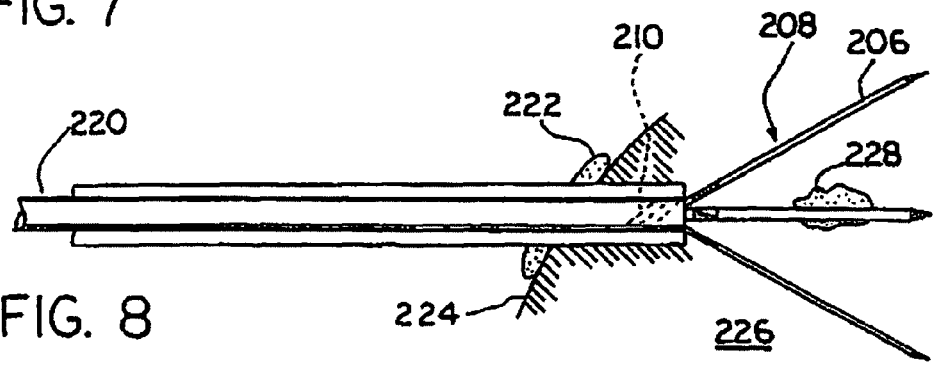
FIG. 8 is a side view of the apparatus illustrated in FIG. 7 showing the support struts deployed.
Figure 9:
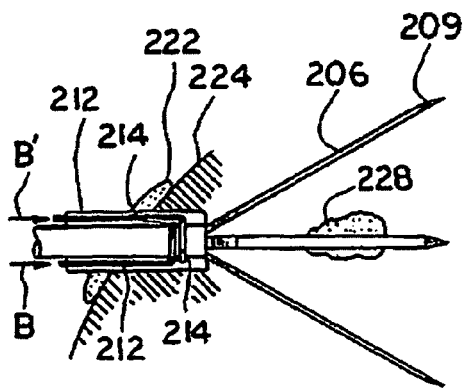
FIG. 9 is a side view of the preferred embodiment of the apparatus showing the struts deploying about a percutaneous growth.
Figure 10:
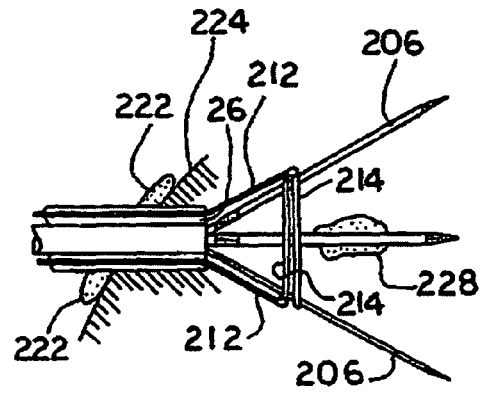
FIG. 10 is a side view of the preferred embodiment of the apparatus showing advancement of the cutting wire along a strut margin.

In the preferred embodiment shown in FIG. 6, a plurality of guide struts generally designated 150 are advanced through a skin surface incision 126 and past a target tissue mass 115 via a tubular housing defining an extrication channel 26. As shown in FIGS. 7 and 8, guide struts 150 are inserted through surface incision 126 and moved to a position to define a conically shaped desired excision margin 100 respecting the target tissue mass 115, shown in FIG. 11. As shown in FIGS. 8 through 10, the extension and configuration of struts 150 from surface incision 126 past target mass 115 creates a gradually expanding subcutaneous retrieval path referred to as a conical penumbra 95.

As shown in FIGS. 11 through 13, an electro-cauterizing cutting snare 155 is advanced along guide struts 150, creating a conically shaped excision margin.

Figure 15:
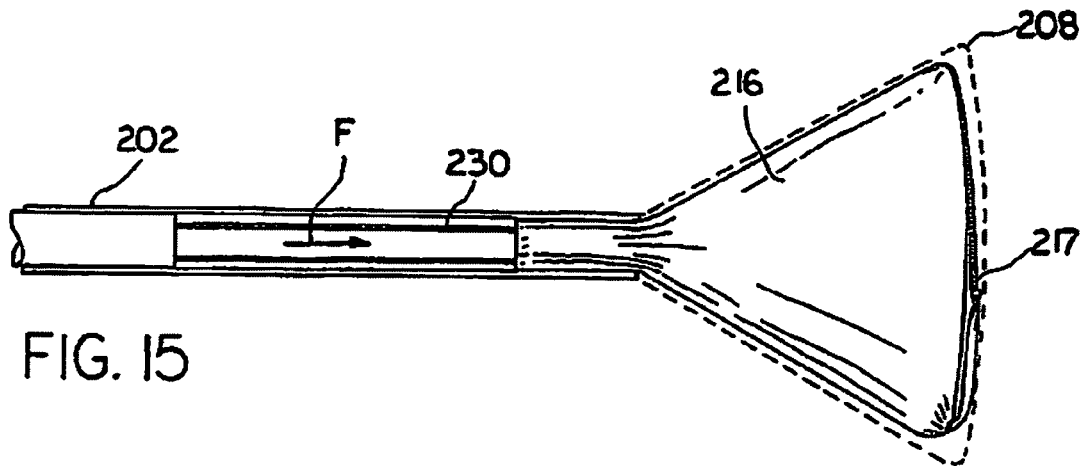
FIG. 15 is a side view of the preferred embodiment of the apparatus showing the containment sheath deploying.
Figure 16:
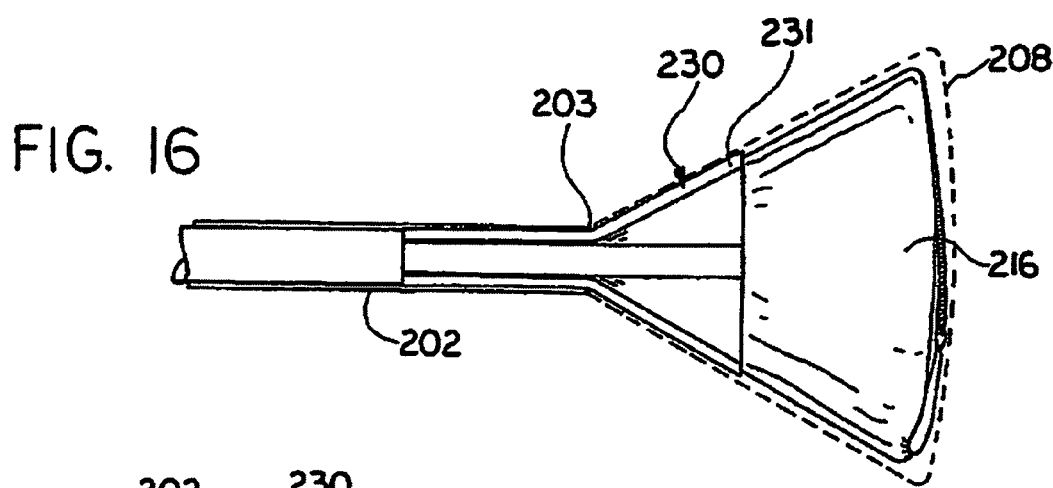
FIG. 16 is a side view of the preferred embodiment of the apparatus showing the containment sheath normally deployed.
Figure 17:
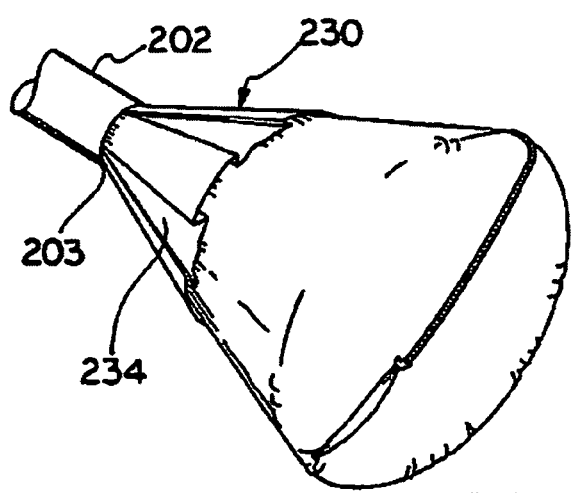
FIG. 17 is an isometric view of the apparatus shown in FIG. 16.
Figure 18:
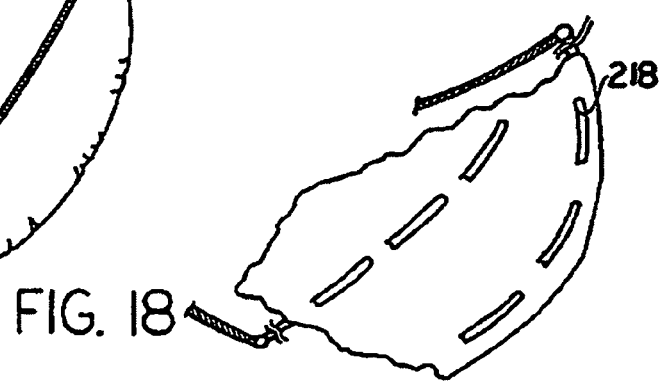
FIG. 18 is a broken view of the tissue containment bag showing the drawstring tissue.

Referring to FIG. 14, the cutting snare 155 is advanced beyond the length of the guide struts 150 to where cutting snare 155 is drawn closed by pulling an integral drawstring 160 towards the exterior of the skin. As shown in FIGS. 15 through 17, mouth 27 of sheath 25 is advanced along the defined extrication channel 26 and expanded by pulling the polyvinyl pull tab which is not shown. As shown in FIGS. 18 through 24, guide struts 150 are enveloped by snaring sheath 25 and may be removed from subcutaneous cavity through extrication channel 26.

In one preferred practice of the invention as depicted in FIGS. 6 through 27 and using the apparatus shown therein, apparatus 200 includes a support conduit designated generally 202 and axially elongating skin cutting means 204 having a cutting blade 205 which is insertable through support conduit 202 as illustrated generally in FIG. 6. Skin cutting means 204 and particularly cutting blade 205 to make a suitable incision in the skin, preferably in the human breast designated generally 246 in FIG. 24 where the skin is designated 224 in the drawing figures including FIG. 6 and FIG. 24. The incision is made to provide access to a target tissue mass designated generally 228 in the drawings which has been previously identified preferably using x-ray mammographic techniques as being dangerous and hence to be removed.

Once a skin incision, designated generally 248 in the drawings, has been made by skin cutting means 204 and appropriate use of cutting blade 205 thereof, skin cutting means 204 is preferably withdrawn axially through support conduit 202, moving to the left in FIG. 6, and support means designated generally 207 and having a plurality of support members designated generally 206 is inserted axially through support conduit 202 and into the sub-cutaneous tissue 226 of the breast as indicated generally in FIG. 7, with the direction of travel of support means 207 indicated generally by arrow A in FIG. 7.

As support members 206 of support means 207 are inserted into the sub-cutaneous tissue 226, support members expand 206 radially due to influence of resilient spring means 210, illustrated in dotted lines in FIG. 8 and forming a portion of support means 207 to a position where support members 206 define a conical penumbra enveloping target tissue mass 228. The conical penumbra 208 defines planes of incision for removal of target tissue mass 228 and a medically advisable amount of surrounding sub-cutaneous healthy tissue 226.

As support members 206 radially diverge one from another due to the influence of resilient spring means 210, remote tips 209 of support members 206 define a circle which in turn defines the base of conical penumbra 208. Remaining, proximate ends of support members 206 are pivotally connected to a supporting shaft, not numbered in the drawings, for pivoting rotation thereabout in response to spring 210.

Once support members 206 have been deployed, into the position illustrated in FIG. 8, the target tissue mass is well within the conical penumbra defined by support members 206.

A pair of tissue cutting wire loops 214 are positioned about the bases of support members 206, as illustrated generally in FIG. 9, and are supported by and emerge from respective support catheters 212, also illustrated in FIG. 9. Support catheters 212 are sufficiently rigid that when force is applied in the axial direction to support catheters 212 is indicated by arrows B and B' in FIG. 9, support catheters 212 move to the right in FIG. 9 advancing tissue cutting wire loops 214 along the outer periphery of support members 204 as depicted generally in FIG. 10.

As support catheters 212 are moved to the right in FIGS. 9 and 10, additional lengths of tissue cutting wires 214 is supplied through support catheters 212 so that tissue cutting wires 214, which are in the form of loops about the exterior surfaces of support members 206 as illustrated in FIG. 10, can enlarge as the circumference of the conical penumbra, measured about the slant surface of the conical penumbra defined by support members 206 as illustrated in FIG. 10, increases.

Support catheters 212 are urged to the right in FIG. 10 until tissue cutting wire loops 214 pass the remote tips 209 of support members 206 and define a pair of essentially coincident and in any event concentric circles forming the base of conical penumbra 208.

Once tissue cutting wire loops 214 have reached this position due to movement of support catheters 212, the wire forming tissue cutting wire loops 214 are drawn to the left, through respective support catheters 212. This causes the respective tissue cutting wire loops 214 each to cinch together as the wires are withdrawn as indicated generally by arrows C, C' in FIG. 11. As the tissue cutting wires are drawn to the left in FIG. 11 through respective support catheters 212, the wire loops each cinch together thereby cutting circular incisions through the sub-cutaneous tissue; this action is illustrated generally in FIG. 11 where the respective tissue cutting wire loops are shown partially, but not completely, cinched. Two wire loops are preferable, for symmetrical application of force.

Once tissue cutting wire loops 214 have been completely cinched and the wires withdrawn to the position illustrated in FIG. 12 by continually drawing the respective tissue cutting wires 214 in the directions indicated by arrows D, D' in FIG. 12, the conical penumbra 208 defines planes of incision created by action of tissue cutting wire loops 214 where those planes of incision are shown in dotted lines in FIG. 12. Note that two dotted lines are shown at the extreme right of FIG. 12 to indicate that two circular planar incisions created by action of respective tissue cutting wire loops 214. Desirably, these two circular planar incisions are essentially congruent one with another.

Once tissue cutting wire loops 214 have been completely withdrawn into the position illustrated in FIG. 12, a suitable tissue containment bag structure 216 is advanced outwardly of support conduit 202, around the outer periphery of support means 207 and particularly support members 206. Tissue containment bag 216 preferably has a pair of drawstrings 218, which may be metal, suture material, suitable plastic monofilaments and the like, which are sewn or threaded into tissue containment bag 216 proximate the vertical right-hand margin thereof appearing in FIG. 13. Drawstrings 218 have extremity portions 219 illustrated in FIG. 13.

Once tissue containment bag 216 has been advanced so that its margin 217 has traveled inwardly with respect to the breast past the remote tips 209 of members 206, to the position generally corresponding to the base of conical penumbra 208, drawstring extremities 219 are pulled to the right in FIGS. 13 and 14, thereby causing looped drawstrings 218, 218' to close margin 217 of bag 216, causing margin 217 to circularly gather as shown in FIG. 14.

Once margin 217 of bag 216 has been circularly gathered thereby effectively closing bag 216 about the target tissue mass 228 of interest, an expandable sheath 230 is advanced through the interior of support conduit 202 about tissue containment bag 216 with expandable sheath 230 moving in the direction indicated by arrow F in FIG. 15. Expandable sheath 230 has a pleated expandable portion 231, which is resilient and seeks to expand radially outwardly to relieve internal stresses such that upon expandable portion 231 reaching terminus 203 of support conduit 202 which is within sub-cutaneous tissue 226, expandable portion 231 expands radially into the configuration illustrated generally in FIG. 16. Expandable portion 231 of sheath 230 is preferably pleated, as depicted in FIG. 17.

Expandable sheath 230 and particularly expandable portion 231 thereof provides support in the form of radially inwardly directed force on tissue containment bag 216 as bag 216 with target tissue mass 228 enveloped therein is pulled to the left in FIGS. 16, 19 and 20 as indicated generally by arrows G in FIG. 19 and arrow H in FIG. 20. The radially inward force provided on tissue containment bag 216 and target tissue mass 228 contained therein by expandable sheath 230, as tissue containment bag 216 is pulled to the left in FIG. 19, compresses tissue mass 228 into a smaller volume and essentially squashes tissue mass 228 into a longitudinally elongated form for passage through support conduit 202. Application of the radial force to tissue mass 228 reduces the transverse cross-sectional dimension of tissue mass 228 to at least the diameter of support conduit 202 as tissue containment bag 216 is drawn through the funnel-shaped expandable portion 231 of sheath 230 and into the interior of support conduit 202.

Once bag 216 and tissue mass 228 contained therein have been removed from the sub-cutaneous tissue, expandable sheath 230 may be removed by pulling it in the direction indicated by arrow H in FIG. 20.

Optionally, while expandable sheath 230 is in position and perhaps only part way removed from the resected area of interest, a medicament bag 232 may be inserted into the resected area through the interior of support conduit 202 and through expandable sheath 230, as indicated in FIG. 21. This may provide means for supplying radioactive gas to provide radiation therapy to the resected area. Additionally, a radiographic marker depicted as 236 may be implanted into the resected area of interest, using the balloon or otherwise while expandable sheath 230 remains in the area of the resection. As an additional option while expandable sheath remains in position thereby maintaining a void in the resected area of the sub-cutaneous tissue, liquid medication indicated schematically as 234 in FIG. 22 may be supplied to the resected area. In such case expandable sheath maintaining the resected tissue in a spaced-apart condition facilitates application of the liquid medication to all parts of the resected volume.

Figure 24:
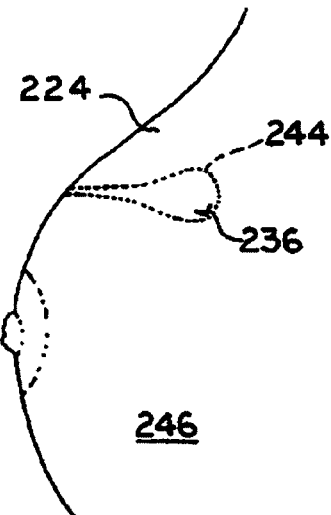
FIG. 24 depicts the female breast and illustrated the incision resulting from practice of the method.
Figure 25:
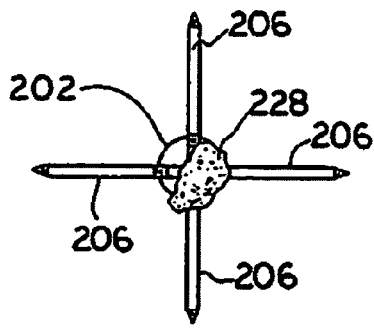
FIG. 25 is partial end elevation taken looking from the right in FIG. 8.
Figure 26:
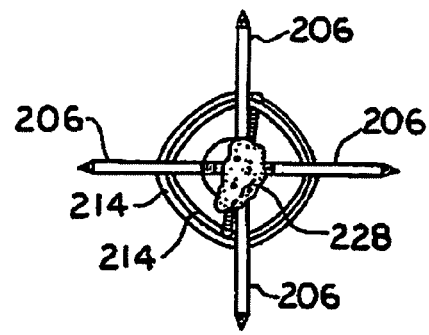
FIG. 26 is partial end elevation taken looking from the right in FIG. 10.
Figure 27:
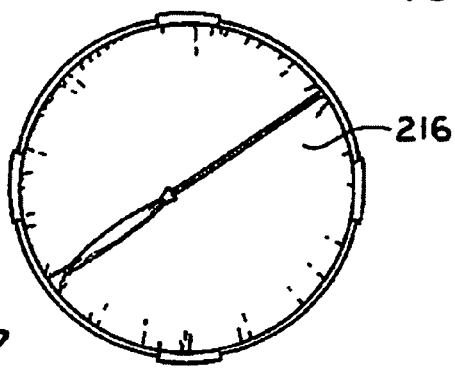
FIG. 27 is partial end elevation taken looking from the right in FIG. 16.

Utilizing the method and apparatus as described hereinabove results in a small, tunnel like incision approaching the skin of the breast with a larger, resected mass being removed therefrom; the resulting internal incision is depicted 244 in FIG. 24.

Figure 23:
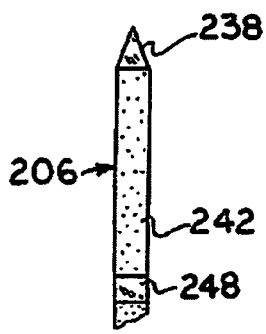
FIG. 23 is an elevation of a support member.

Support members 206 preferably have metallic tips to provide radiopaque characteristics as indicated by 230 in FIG. 23 and may also have metallic or other radiopaque marker bands indicated as 248 in FIG. 23. Central portions 242 of support members 206 are preferably radiolucent as indicated by the stippling in FIG. 23.

Figure 29:
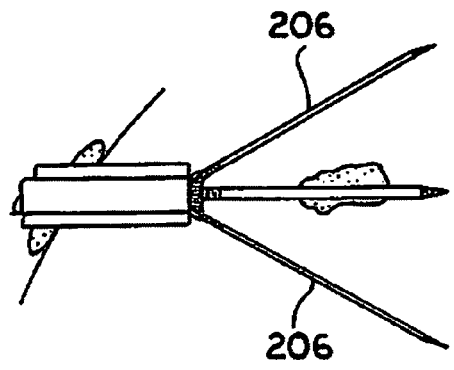
FIG. 29 is a partially sectioned side elevation of the embodiment of apparatus illustrated in FIG. 28 prior to deployment of the hook and rod structure facilitating simultaneous performance of the cutting and bagging steps.
Figure 30:
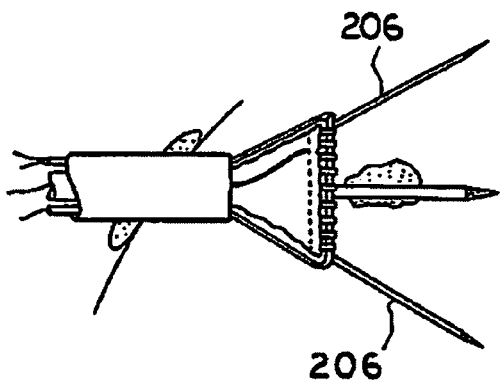
FIG. 30 is a partially sectioned side elevation of the embodiment of apparatus illustrated in FIG. 28 showing deployment of the hook and rod structure facilitating simultaneous performance of the cutting and bagging steps.
Figure 28:
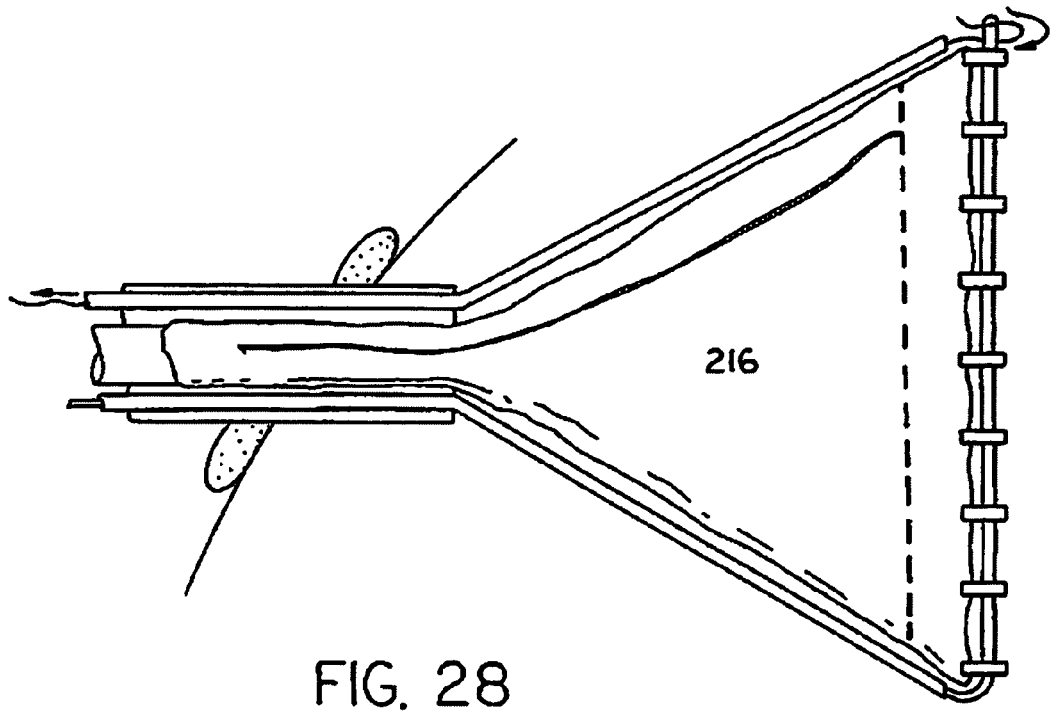
FIG. 28 is a side elevation of a second preferred embodiment of apparatus embodying the invention with hook and rod structure facilitating simultaneous performance of the cutting and bagging steps.

In FIGS. 28 through 30 the curing wire and bag are connected by hook and rod structure as illustrated.

I claim the following:

1. A surgical biopsy apparatus comprising:
   a sheath housing having a distal portion and a longitudinal axis;
   an array of cutting blades; and
   a shaft positioned in the sheath and having a longitudinal axis and an interior channel, the shaft extending distally through the array of cutting blades, the interior channel dimensioned to deliver a marker to the incision site, the cutting blades expandable radially with respect to the shaft to a second expanded position, the cutting blades being rotatable in the second position to cut tissue, wherein the interior channel delivers a marking fluid to the tissue to mark the excision site.

2. The apparatus of claim 1, further comprising a tissue collection member for capturing the cut tissue.

3. The surgical biopsy apparatus of claim 2, wherein the tissue collection member has a distally oriented opening and is advanceable distally from the housing.

4. The apparatus of claim 3, wherein the tissue collection member is advanceable subsequent to movement of the cutting blades to the expanded position.

5. The apparatus of claim 3, wherein the tissue collection member is expandable by the cutting blades as it passes distally over an outer surface thereof so the distally oriented opening of the tissue collection member expands to a transverse dimension exceeding a transverse dimension of the sheath, and thereafter reduces in transverse dimension upon continued advancement.

6. The apparatus of claim 2, wherein the tissue collection member is initially retained in the housing in a collapsed position.

7. The apparatus of claim 6, wherein the tissue collection member has an inner surface coaxial with the shaft.

8. The apparatus of claim 1, further comprising a tissue piercing member for enabling the sheath to penetrate tissue.

9. The apparatus of claim 2, wherein the tissue collection member has an inner surface coaxial with the shaft.

10. The apparatus of claim 3, further comprising a drawstring connected to the tissue collection member for closing the tissue collection member.

11. The apparatus of claim 1, wherein the array of cutting blades forms a circular array.

12. The apparatus of claim 1, wherein the cutting blades move to the expanded position in response to distal movement of the shaft.

13. The apparatus of claim 1, wherein the shaft is linked with an electric motor.

14. The apparatus of claim 8, wherein the cutting blades are positioned proximal of the tissue piercing member.

* * * * *